(12) United States Patent
Thoen et al.

(10) Patent No.: US 9,310,263 B2
(45) Date of Patent: Apr. 12, 2016

(54) ADIABATIC SCANNING CALORIMETER

(75) Inventors: Jan Thoen, Blanden (BE); Christ Glorieux, Heverlee (BE); Jan Leys, Lille (BE)

(73) Assignee: Katholieke Universiteit Leuven, Leuven (BE)

( * ) Notice: Subject to any disclaimer, the term of this patent is extended or adjusted under 35 U.S.C. 154(b) by 485 days.

(21) Appl. No.: 13/808,278

(22) PCT Filed: Jul. 7, 2011

(86) PCT No.: PCT/BE2011/000042
§ 371 (c)(1),
(2), (4) Date: Jan. 4, 2013

(87) PCT Pub. No.: WO2012/003553
PCT Pub. Date: Jan. 12, 2012

(65) Prior Publication Data
US 2013/0121369 A1    May 16, 2013

(30) Foreign Application Priority Data

Jul. 8, 2010   (GB) .................................. 1011522.8
Sep. 9, 2010   (GB) .................................. 1014995.3

(51) Int. Cl.
*G01K 17/00* (2006.01)
*G01K 17/04* (2006.01)
*G01N 25/48* (2006.01)

(52) U.S. Cl.
CPC ................ *G01K 17/00* (2013.01); *G01K 17/04* (2013.01); *G01N 25/4833* (2013.01)

(58) Field of Classification Search
CPC combination set(s) only.
See application file for complete search history.

(56) References Cited

U.S. PATENT DOCUMENTS

| 3,888,726 A | | 6/1975 | Hultman | |
| 4,255,961 A | * | 3/1981 | Biltonen et al. | ................. 374/11 |
| 5,741,068 A | * | 4/1998 | Hemmerich et al. | ........... 374/31 |
| 5,813,763 A | * | 9/1998 | Plotnikov et al. | ................ 374/11 |
| 2010/0303124 A1 | * | 12/2010 | Ellison et al. | ................... 374/31 |

OTHER PUBLICATIONS

International Search Report and Written Opinion mailed Nov. 24, 2011 in connection with International Application No. PCT/BE2011/000042, filed Jul. 7, 2011.
Thoen J et al, "Investigations of phase transitions in liquid crystals by means of adiabatic scanning calorimetry", Liquid Crystals, Taylor & Francis Ltd., UK, vol. 36, No. 607, Jun. 2009, pp. 669-684.

(Continued)

*Primary Examiner* — Lisa Caputo
*Assistant Examiner* — Nasir U Ahmed
(74) *Attorney, Agent, or Firm* — Duane Morris LLP; Gregory M. Lefkowitz

(57) ABSTRACT

The present invention generally relates to an adiabatic scanning calorimeter for simultaneous measurements of the temperature dependence of heat capacity and enthalpy of liquids and solids and phase transitions therein. Moreover, the invention allows for an accurate separation between pretransitional enthalpy variations and true latent heats at first-order or weakly first-order phase transitions. In addition, the invention relates to calorimeters for controlling temperature differences and heat fluxes in different modes of operation.

41 Claims, 13 Drawing Sheets

(56) References Cited

OTHER PUBLICATIONS

Pilcher et al, "A simplified; calorimeter for the precise determination of purity", Analytica Chimica ACTA, Elsevier, Amsterdam, NL, vol. 17, Jan. 1, 1957, pp. 144-160.

Inaba, H et al, "Nano-Watt Stabilized DSC and its Applications", Journal of Thermal Analysis and Calorimetry, Kluwer Academic Publishers, Dordrecht, NL, vol. 79, No. 3. Feb. 1, 2005, pp. 605-613.

* cited by examiner

FIGURE 9 (panels A &B)

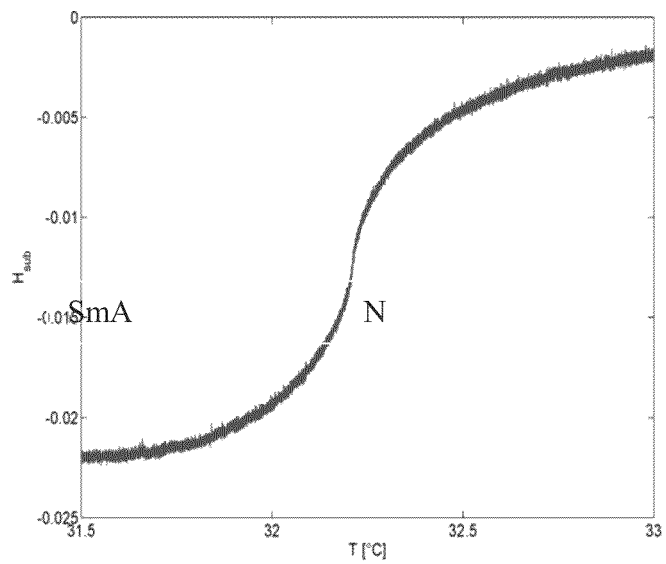
Fig. 14A
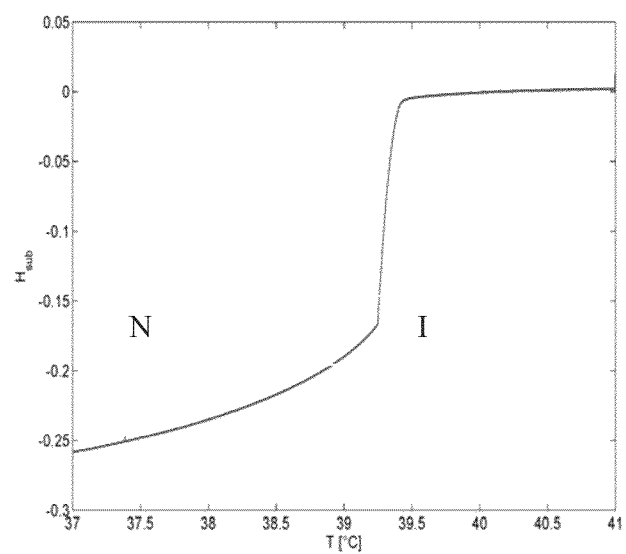
Fig 14B
FIGURE 14

ADIABATIC SCANNING CALORIMETER

CROSS-REFERENCE TO RELATED APPLICATIONS

This application is a §371 national stage entry of International Application No. PCT/BE2011/000042, filed Jul. 7, 2011, which claims priority to Great Britain Patent Application No. 1011522.8 filed Jul. 8, 2010 and Great Britain Patent Application No. 1014995.3 filed Sep. 9, 2010, the entire contents of which are incorporated herein by reference.

BACKGROUND OF THE INVENTION

A. Field of the Invention

The present invention generally relates to an adiabatic scanning calorimeter for simultaneous measurements of the temperature dependence of heat capacity and enthalpy of liquids and solids and phase transitions therein. Moreover, the invention allows for an accurate separation between pretransitional enthalpy variations and true latent heats at first-order or weakly first-order phase transitions. In addition, the invention relates to calorimeters for controlling temperature differences and heat fluxes in different modes of operation.

B. Description of the Related Art

Measurements of the heat capacity and enthalpy changes play an important role in monitoring the energy content of condensed matter systems. As such calorimetry is an indispensable technique for many scientific fields. Depending on the application envisioned several different technical approaches with varying degrees of accuracy and precision have been developed. Over wide temperature ranges generally the classical Nernst heat pulse method is used.[1] During the last 50 years several new approaches, supported to a large extent by novel developments in electronic measurements instrumentation, have emerged, e.g. differential scanning calorimetry (DSC),[2,3] scanning transitiometry[4-6] and modulation techniques like ac calorimetry[7,8], the 3ω method[9] and more recently photoacoustic and photopyroelectric techniques,[10] Peltier ac and Peltier tip calorimetry,[11,12] Peltier heat-flow and modulated bath ac calorimetry.[13,14]

A novel development beyond classical adiabatic heat pulse calorimetry, took place at the end of the 1960s when Australian scientists[15-17] imposed a very slow constant heating (or cooling) rate on the thermal shield (in a classical type adiabatic calorimeter) surrounding the sample cell and the cell was forced to follow with the same rate. By measuring the imposed rate and the power applied (heating) to or extracted (cooling) from the cell, the heat capacity C is readily obtained from $$C = T\frac{dS}{dT} = \frac{dQ}{dT} = \frac{dQ/dt}{dT/dt} = P/\dot{T}, \quad (1)$$

with S the entropy, T the temperature, dQ the supplied heat, t the time, P the supplied power and $\dot{T}$ the temperature scanning rate. If one considers the shield (forced to change its temperature at constant $\dot{T}$) as the reference 'sample', the setup is conceptually similar to the (power compensated) differential scanning calorimeter. There are, however, basic differences in design principles and area of applications. The DSC is a very useful for many (material science) applications when the (total) energy change of a transition is of greater interest than the detailed form of the specific heat or enthalpy curve (near phase transitions). A commercial DSC (or modulated DSC) generally does not yield accurate absolute values of specific heat and by using high scanning rates (typically above 0.2 $Ks^{-1}$ to have a reasonable sensitivity) quite often operates out of thermodynamic equilibrium, in particular near fluctuations dominated phase transitions. Moreover, with DSC it is often not possible to discriminate between second-order (continuous) phase transitions and (weakly) first-order ones.[18] Several of the limitations of DSCs have been eliminated in scanning transitiometry by imposing very slow constant scanning rates in a high precision differential concept[4-6]. However, imposing constant rates in this approach remains a basic problem for high-resolution work at and near (weakly) first-order transitions. Buckingham and coworkers called their apparatus a high precision scanning ratio calorimeter (for use near phase transitions).[17] In order to cope with the critical slowing down near the investigated liquid-gas critical point, they imposed constant scanning rates as low as $10^{-6}$ $Ks^{-1}$. In the mid 1970s a group at the Catholic University of Leuven (Belgium) built a four stage scanning calorimeter to measure with high resolution the heat capacity (at constant pressure) near critical (consolute) points of binary and ternary liquid mixtures.[19-22] The construction of that calorimeter was such that in addition to different scanning modes it could also be used as a classical step calorimeter. It was also realized that near phase transitions and critical points it would be much easier to cope with the critical slowing down and the large increase of the heat capacity and possible latent heats, by imposing a constant heating or cooling power to the sample and determine the rate instead of imposing a constant heating or cooling rate as was done before, i.e. keeping P constant and not $\dot{T}$ in Equation (1).[20,21] In fact, this change in operation mode is essential for the proper investigation of (weakly) first-order phase transitions.[23,24] It is quite straightforward to show that the direct experimental results of the (constant) power P and the temperature T(t) of the sample as function of the time t (since the start of the run at $T(t_s)$) yields the temperature dependence of the enthalpy (including a value of the latent heat when present) by $$H(T) = H(T_s) + P(t - t_s) \quad (2)$$

Around that time, calorimeters similar to the Leuven adiabatic scanning type calorimeter were developed by other groups as well. In 1980 Würz and Grubić[25] described a three stages adiabatic calorimeter of the scanning ratio type and did measurements at constant scanning rates of 128.8 $\mu Ks^{-1}$ and 6.98 $\mu Ks^{-1}$ near a liquid-liquid critical point, Junod[25] described a setup with a continuous adiabatic (scanning) method for the graphical recording of the heat capacity of solids over the temperature range between 80 K to 320 K at moderate to fast scanning rates (typically around 10 $mKs^{-1}$). A microcomputer controlled ASC type apparatus for solid samples was described in a paper of 1981.[27] After the introduction of adiabatic scanning calorimetry (ASC) for first-order and second-order phase transition studies in liquid crystals[23,24] it was also used for liquid crystal studies by Anisimov and coworkers.[28] Bessergenev et al. used different ASC modes of operation to study first-order and second-order transitions in rear earth metals.[29] Lysek et al. described a scanning ratio calorimeter (at rates of about 1 $mKs^{-1}$) for use in adsorption studies.[30] An ASC technique similar to the Leuven one was used by Sirota to study phase transitions and super cooling of normal alkanes.[31,32] Schnelle and Gmelin introduced a high resolution ASC for small (solid) samples.[33] Moon and Yeong proposed, in 1996, a so-called rate-scanning modified adiabatic calorimeter (MAC) (with scanning rates between 0.2 $mKs^{-1}$ and 30 $mKs^{-1}$).[34,35] However, their setup is operationally the same as the previously well established standard ASCs as used by several other groups. An ASC similar to the Leuven one for the study of liquid-liquid critical points was built by Jacobs and collaborators.[36]

An important requirement, of a high-resolution adiabatic calorimeter operating in the heating mode is the equality (better than a mK) of the temperatures of the sample and the surrounding thermal shield. For operations in the cooling mode a constant preset temperature difference between the sample and the shield has to be maintained within the same stability limits. This is presently achieved using thermistors as highly sensitive resistance thermometers placed on the sample and on the shield. Before these sensors can be used, time consuming extensive calibrations (against reference thermometers) have to be executed. Moreover, the temperature coefficients of the resistance of two thermistors do never perfectly match. Via hardware adaptations in the measuring circuits[23] or in software modifications of the calibration curves, one can partly correct for it. The present invention eliminates these problems completely by inserting between the sample and the shield a very sensitive (of the order of 0.1V/K) semi-conductor materials based Peltier element (PE), either a Peltier cooler or Peltier thermogenerator, which are commercially available. The μK sensitivity of the PE for temperature differences allows in combination with proper servo systems (hardware or software) to maintain almost perfect equality of the sample and shield temperatures in the heating mode. For the cooling mode a preset temperature difference between sample and shield can be kept constant with equal resolution.

SUMMARY OF THE INVENTION

The present invention solves the problems of the related art by introducing an adiabatic scanning calorimeter for simultaneous measurements of heat capacity and enthalpy over broad temperature ranges (typically 100K) in different accurately controlled scanning modes by introducing sensitive Peltier elements in the temperature and scanning rate control of different stages in the calorimeter.

In accordance with the purpose of the invention, as embodied and broadly described herein, the invention is broadly drawn to eliminate problems with keeping temperature differences between an investigated sample and a surrounding thermal (adiabatic) shield zero or at a preset fixed value during temperature scanning over broad ranges without approximations and lengthy calibrations inherently associated in using different separate temperature sensors as in the previous art.

In one aspect of the invention it is possible in the two principal (heating or cooling) scanning modes of operation of the calorimeter to simultaneously arrive at accurate and detailed information on the temperature dependence of the heat capacity and enthalpy by delivering constant heating or cooling power to the sample and by Peltier element based control of the thermal shield. The thus operated calorimeter allows for a clear separation of pretransitional enthalpy increases and true latent heats at (weakly) first-order transitions and precise characterization of heat capacity anomalies at second-order phase transitions.

An other aspect of the calorimeter is the possibility to operate, besides in the above mentioned principal modes, in several other more conventional or unconventional ways, as e.g. in DSC-like constant heating or cooling rate modes, as a classical (Nernst-type) heat pulse step calorimeter, in the two principal modes without sensor or heater attached to the sample, or in modulated heating or cooling power modes, or in purely ac heating or cooling modes.

Still another aspect of the invention is the versatility in arranging the sample (liquid or solid) configurations to adapt to the chosen scanning modes.

In still another aspect of the invention, the full implementation of programmable electronic measurement and control equipment connected to a personal computer allows full software choice of operational modes, long term independent operation and extensive data analysis.

Some embodiments of the invention are set forth directly below:

A particular embodiment of present invention concerns an adiabatic scanning calorimeter apparatus comprising at least one Peltier element [6] and one sample [1] on the sample holder [2], at least one heater [3], at least one thermal or adiabatic shield [8][9] surrounding the sample [1] or sample holder [2], characterised in that the adiabatic scanning calorimeter is for simultaneous measurements of the temperature dependence of heat capacity and enthalpy of solid or liquid samples [1] and phase transitions therein where at least one Peltier element [6], used as a differential thermometer, is placed between the sample or sample holder and the shield and makes good mechanical and thermal contacts with the sample or sample holder and the shield so that a constant preset temperature difference (e.g. fixed temperature difference of a few tenths of a degree) or a zero difference between the sample or sample holder and the shield is maintained. In a more particular embodiments this diabatic scanning calorimeter apparatus has the Peltier element [6] arranged to geometrically position between said at least one plate that contacts the sample [1] or sample holder [2] or adaptor piece [28] and at least one plate that contacts the shield [8] or [9] for instance the shield bottom [8]. Moreover in the apparatus of such embodiments, the sample holder [2] can be positioned in thermal conductive contact with a top plate [5] of the Peltier element [6] and the base plate [7] of the Peltier element [6] is also positioned in good thermal contact with the shield bottom [8].

In any of this above described embodiment the Peltier element can, when in operation, acts as a differential thermometer for controlling the temperature and the scanning rate of the different stages in the calorimeter. Furthermore the at least one sample holder [2] comprises at least one temperature sensor [4] on the sample holder [2].

The apparatus of any of the above described embodiments, can comprise at least one thermal or adiabatic shield [8 or 9] surrounding a sample or sample holder comprises at least one temperature sensor [12] on the shield [8 or 9].

The apparatus of any of the previous embodiments can comprise the shield sensor in the shield or shield bottom [8].

The apparatus of any of the previous embodiments can be is an adiabatic scanning type calorimeter (ASC).

Yet another embodiment of present invention is an apparatus of any of the previous embodiments, whereby the active device is a differential detector thermocouple. Hereby the Peltier element or Peltier diode can be provided with either cooler or thermogenerator function or the Peltier element or Peltier diode or thermopile is a zero instrument.

Yet another embodiment of present invention is an apparatus of any of the previous embodiments, whereby the mechanical contact is for heat transfer. Yet another embodiment of present invention is an apparatus of any of the previous embodiments, whereby the temperature sensor is a thermistor.

Yet another embodiment of present invention is an apparatus of any of the previous embodiments, whereby the temperature sensor is a Platinum resistance thermometer.

Yet another embodiment of present invention is an apparatus of any of the previous embodiments, whereby at least one temperature sensor is placed on an adaptor piece and on the shield.

Yet another embodiment of present invention is an apparatus of any of the previous embodiments, whereby the sample is a liquid in a sample holder.

Yet another embodiment of present invention is an apparatus of any of the previous embodiments, whereby the sample is a solid in a sample holder or in direct thermal contact with the Peltier element.

Yet another embodiment of present invention is an apparatus of any of the previous embodiments, whereby the sample holder is placed in an adaptor piece.

Yet another embodiment of present invention is an apparatus of any of the previous embodiments, whereby the apparatus is provided with a controller with servo systems (hardware or software) to maintain almost perfect equality of the sample and shield temperatures in the heating mode based on the readings of the Peltier element.

Yet another embodiment of present invention is an apparatus of any of the previous embodiments, whereby when operational the controller and the Peltier element keep the temperature differences between an investigated sample and a surrounding thermal or adiabatic shield zero or at a preset fixed value during temperature scanning over broad ranges without the need to rely on approximations and calibrations of the separate temperature sensors.

Yet another embodiment of present invention is an apparatus of any of the previous embodiments, whereby the temperature difference between sample and shield can be kept constant.

Yet another embodiment of present invention is an apparatus of any of the previous embodiments, whereby when operational the Peltier element keeps the temperature difference between the shield and the sample that is analyzed on zero or at a constant temperature difference during the whole temperature range.

Yet another embodiment of present invention is an apparatus of any of the previous embodiments, whereby the apparatus when operational in the heating mode maintains equality of the temperatures of the sample and the surrounding thermal shield.

Yet another embodiment in present invention is the apparatus of any of the previous embodiments, which comprises an assembly of multiple units each with sample holder, thermal or adiabatic shield and active Peltier element that mechanically contacts a sample or sample holder and a shield for simultaneously measuring the temperature dependence of heat capacity and the enthalpy of a sample and of phase transitions therein. Hereby the multiple units are connected to a signal processor and input signals from each unit can be fed to said signal processor with a controller that controls the Peltier elements.

Yet another embodiment of present invention is an apparatus of any of the previous embodiments, where the sample and adiabatic shield are surrounded by additional thermal shields, each with temperature sensors and heaters under the control of a servo system on a processor.

Yet another embodiment of present invention is an apparatus of any of the previous embodiments, where the number of thermal shields or Peltier elements is varied.

Yet another embodiment of present invention concerns the use of the apparatus of any of the previous embodiments, where a constant heating power is delivered to the sample and/or to the sample holder.

Yet another embodiment of present invention concerns the use of the apparatus of any of the previous embodiments, where a constant cooling power is delivered to the sample and/or to the sample holder.

Yet another embodiment of present invention concerns the use of the apparatus of any of the previous embodiments, where the heat transfer through the Peltier element is used to heat the sample.

Yet another embodiment of present invention concerns the use of the apparatus of any of the previous embodiments, where the heat transfer through the Peltier element is used to cool the sample.

Yet another embodiment of present invention concerns the use of the apparatus of any of the previous embodiments, where the heating power to the sample is modulated.

Yet another embodiment of present invention concerns the use of the apparatus of any of the previous embodiments, where the cooling power to the sample is modulated.

Yet another embodiment of present invention concerns the use of the apparatus of any of the previous embodiments, where the calorimeter can be evacuated.

Yet another embodiment of present invention concerns the use of the apparatus of any of the previous embodiments, where the calorimeter can be filled with a chosen gas.

Yet another embodiment of present invention concerns the use of the apparatus of any of the previous embodiments, for simultaneously in one scan measuring in a thermodynamic equilibrium the heat capacity and enthalpy of phase transition of a sample.

Yet another embodiment of present invention concerns the use of the apparatus of any of the previous embodiments, for simultaneous measurements of heat capacity and enthalpy of phase transitions by an operation in thermodynamic equilibrium, in particular near fluctuations dominated phase transitions.

Yet another embodiment of present invention concerns the use of the apparatus of any of the previous embodiments, for separation between pretransitional enthalpy of transition variations and true latent heats at first-order or weakly first-order phase transitions.

Yet another embodiment of present invention concerns the use of the apparatus of any of the previous embodiments, which operates in thermodynamic equilibrium for simultaneously in one scan measuring heat capacity and enthalpy of phase transitions of a sample.

Yet another embodiment of present invention concerns the use of the apparatus of any of the previous embodiments, to yield accurate absolute values of specific heat of a sample by using slow scanning rates, in particular below 0.2 $Ks^{-1}$.

Yet another embodiment of present invention concerns the use of the apparatus of any of the previous embodiments, to discriminate between second-order (continuous) phase transitions and (weakly) first-order phase transition of a sample.

Yet another embodiment of present invention concerns the use of the apparatus of any of the previous embodiments, for in one scan defining or characterizing of a phase transition of a material as influence of a production process.

Yet another embodiment of present invention concerns the use of the apparatus of any of the previous embodiments, for in one scan defining or characterizing of a phase transition in liquid crystals.

Yet another embodiment of present invention concerns the use of the apparatus of any of the previous embodiments, for in one scan defining or characterizing of a phase transition on biological systems.

Yet another embodiment of present invention concerns the use of the apparatus of any of the previous embodiments, for in one scan defining or characterizing of a phase transition in cell membranes.

Yet another embodiment of present invention concerns the use of the apparatus of any of the previous embodiments, for in one scan defining a suitable material for a defined property.

Yet another embodiment of present invention concerns the use of the apparatus of any of the previous embodiments, for in one scan selecting a suitable material for a use.

Yet another embodiment of present invention concerns the use of the apparatus of any of the previous embodiments, for monitoring the energy content of a condensed matter sample by quantifying in one scan in thermodynamic equilibrium simultaneously the temperature dependence of the heat capacity and of enthalpy of a sample and of phase transitions therein, the method involving 1) delivering constant heating or cooling power to the sample and by a Peltier element keeping temperature differences between an investigated sample and its surrounding thermal shield zero or at a preset fixed value during temperature scanning over broad ranges with out approximations.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention.

REFERENCES RELEVANT TO THIS APPLICATION

1. W. Nernst, *Ann, Phys.*, 1911, 36, 395.
2. M. J. O'Neill, *Anal Chem.*, 1964, 36, 1238.
3. B. Wunderlich, *Thermal Analysis*, 1990, Academic Press, San Diego.
4. S. L. Randzio, *Thermochim. Acta*, 1985, 89, 215.
5. S. L. Randzio, J.-P., E. Grolier, and J. R. Quint, *Cal. Anal, Therm.*, 1990, 20-21, 315.
6. S. L. Randzio, *Chem. Soc. Rev.*, 1996, 25, 383.
7. P. Sullivan and G. Seidel, *Phys. Rev.*, 1968,173, 679.
8. C. W. Garland, *Thermochim. Acta*, 1985, 88, 127.
9. N. Birge and S. Nagel, *Phys. Rev. Lett.*, 1985, 54, 2674.
10. J. Thoen and C. Glorieux, Chapter 12 in "Heat capacities: liquids, solutions and vapours", Eds. E. Wilhelm and T. M. Letcher (The Royal Society of Chemistry, London 2010) pp 264-286, and references therein.
11. Y. H. Jung, I. K. Moon, and Y. H. Jeong, *Thermochim. Acta*, 2002, 391, 7.
12. Y. J. Yun, D. H. Jung, I. K. Moon, and Y. H. Jeong, *Rev. Sci. Instrum.* 2006, 77, 064901.
13. T. Plackowski, Y. Wang, and A. Junod, *Rev. Sci. Instrum.*, 2002, 73, 2755.
14. R. Lortz, S. Abe, Y. Wang, F. Bouquet, U, Tutsch, and A. Junod, *Rev. Sci. Instrum.*, 2005, 76, 103902.
15. C. Edwards, J. A. Lipa, and M. J. Buckingham, *Phys. Rev. Lett.*, 1968, 20, 496.
16. J. A. Lipa, C. Edwards, and M. J. Buckingham, *Phys. Rev, Lett.*, 1970, 25, 1086.
17. M. J. Buckingham, C. Edwards, and J. A. Lipa, *Rev. Sci. Instrum.*, 1973, 44, 1167.
18. J, Thoen in *Physical Properties of Liquid Crystals*, D. Demus, J. Goodby, G, Gray, H.-W. Spiess, and V. Vill, Eds, 1997, Wiley-VCH, Weinheim, pp. 208-232.
19. J. Thoen, E. Bloemen, and W. Van Dael, *J. Chem. Phys.*, 1978, 68, 735.
20. E. Bloemen, Ph. D. Thesis, 1979, Katholieke Universiteit Leuven, Belgium
21. E. Bloemen, J. Thoen, W. Van Dael, *J. Chem. Phys.*, 1980, 73, 4628.
22. E. Bloemen, J. Thoen, W. Van Dael, *J. Chem. Phys.*, 1981, 75, 1488.
23. J. Thoen, E. Bloemen, H. Marijnissen, and W. Van Dael, in *Proceedings of the 8th Symposium on Thermophysical properties*, Nat. Bur. Stand., 1981, Maryland, Am. Soc. Yiech. Eng., New York, 1982, pp. 422-428.
24. J, Thoen, H. Marijnissen, and W. Van Dael, *Phys. Rev. A*, 1982, 26, 2886.
25. U. Würz and M. Grabić, *J. Phys. E: Sci. Instrum.*, 1980, 13, 525.
26. A. Junod, *J. Phys. E: Sci. Instrum.*, 1979, 12, 945.
27. P. C. Lancaster and D. P. Baker, *J. Phys. E: Sci. Instrum.*, 1981, 14, 805.
28. M. A. Anisimov, V. P. Voronov, A. O. Kuikov, and F. Kholmurodov, *J. Phys.* (Paris), 1985, 46, 2137.
29. V. G. Bessergenev, Yu. A. Kovalevskaya, I. E. Paukov, and Yu. A. Shkredov *Thermochim. Acta*, 1989, 139, 245.
30. M. Lysek, P. Day, M. LaMadrd, and D. Goodstein, *Rev. Sci. Instrum.*, 1992, 63, 5750.
31. E. B. Sirota and D. M. Singer, *J. Chem. Phys.*, 1994, 101, 10873.
32. E. B. Sirota, *J. Chem. Phys.*, 2000, 112, 492.
33. W. Schnelle and E. Gmelin, *Thermochim. Acta*, 1995, 269/270, 27.
34. I. K. Moon and Y. H. Jeong, *Rev. Sci. Instrum.*, 1996, 67, 3553.
35. Y. H. Jeong, *Thermochim. Acta*, 1997, 304/305, 67.
36. A. C. Flewelling, R. J. Fonseka, N, Khaleeii, J. Partee, and D. T. Jacobs, *J. Chem. Phys.*, 1996, 104, 8048.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

LEGEND TO THE GRAPHICS OF THE APPLICATION

Figure 5:
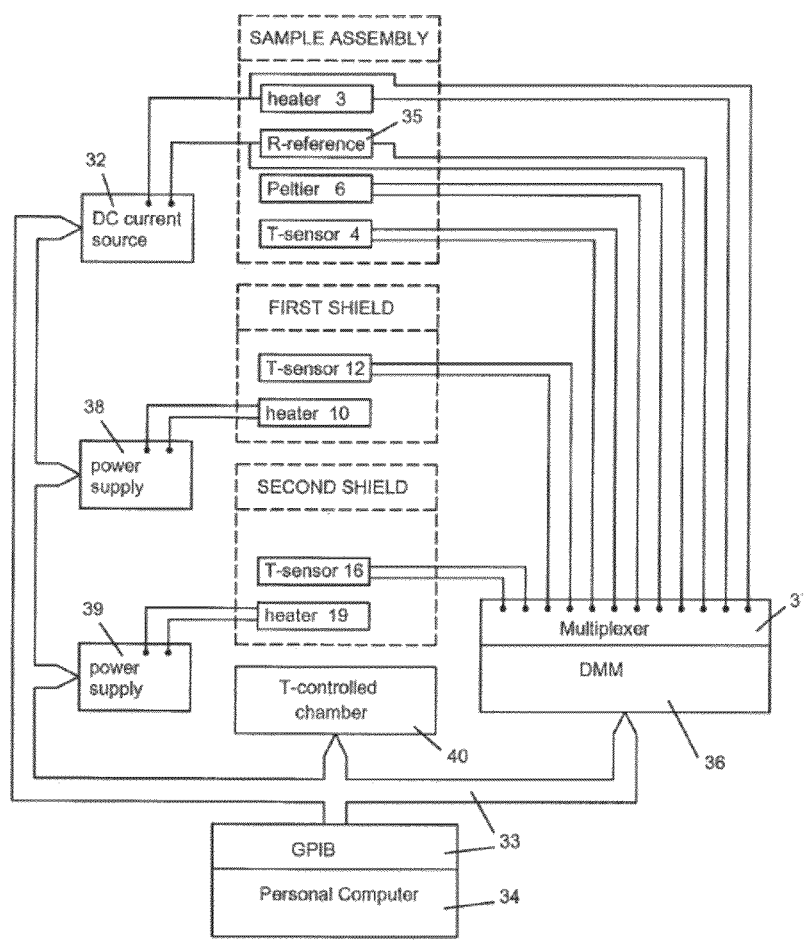

FIG. 5 gives in a schematic representation of the different building blocks used for the proper implementation of the different exemplary modes of operation and of the measurements of the necessary parameters to arrive at the calculation of the temperature dependence of the heat capacity and enthalpy via equations (1) and (2).

Figure 6:
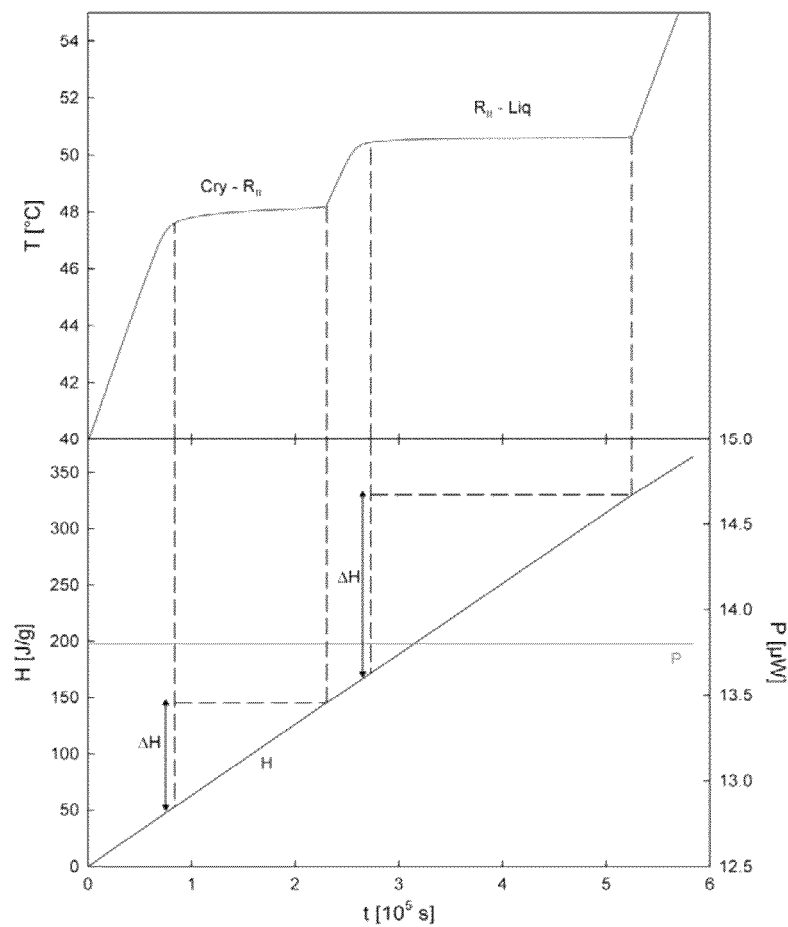

FIG. 6 displays the recorded data as a function of time during a heating run for a 59 mg sample of tetracosane ($C_{24}H_{50}$) with constant power P. The upper panel gives the sample temperature as a function of time. In the lower panel the horizontal line represents the constant power as a function of time and the oblique line gives the enthalpy as a function of time. ΔH represents the latent heat at the two observed first order phase transitions. Cry-$R_{II}$: phase transition between the crystal and the rotator II phase. $R_{II}$-Liq: phase transition between the rotator II and the liquid phase.

Figure 7:
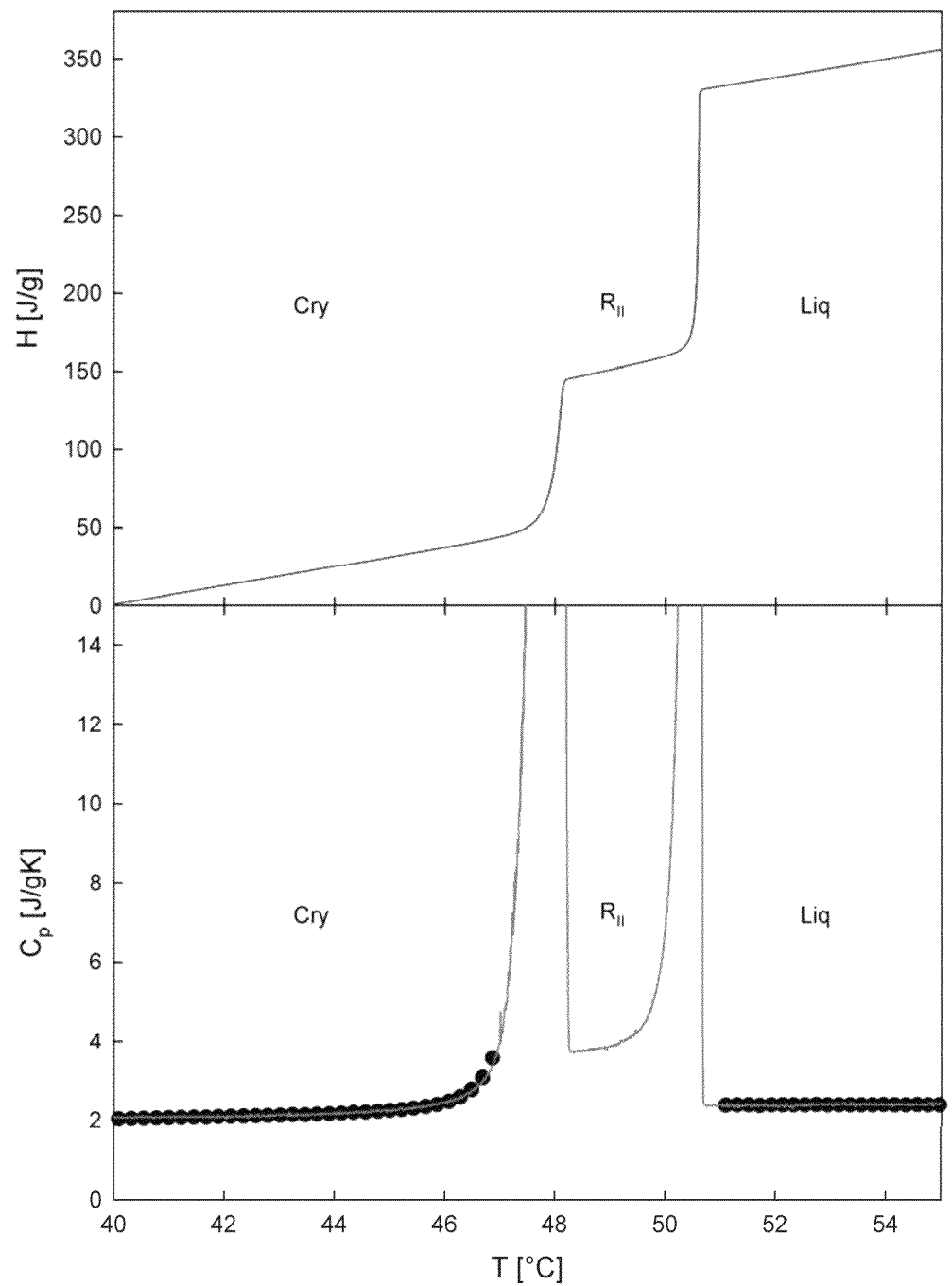

FIG. 7 displays the enthalpy H and heat capacity $C_p$ as a function of temperature as derived from the directly recorded temperature and power data as a function of time.

The solid dots in the lower panel represent heat capacity data of the same sample as obtained by running the pASC in the classical heat step mode.

Cry: crystal phase
$R_{II}$: rotator II phase
Liq: liquid phase

Figure 8:
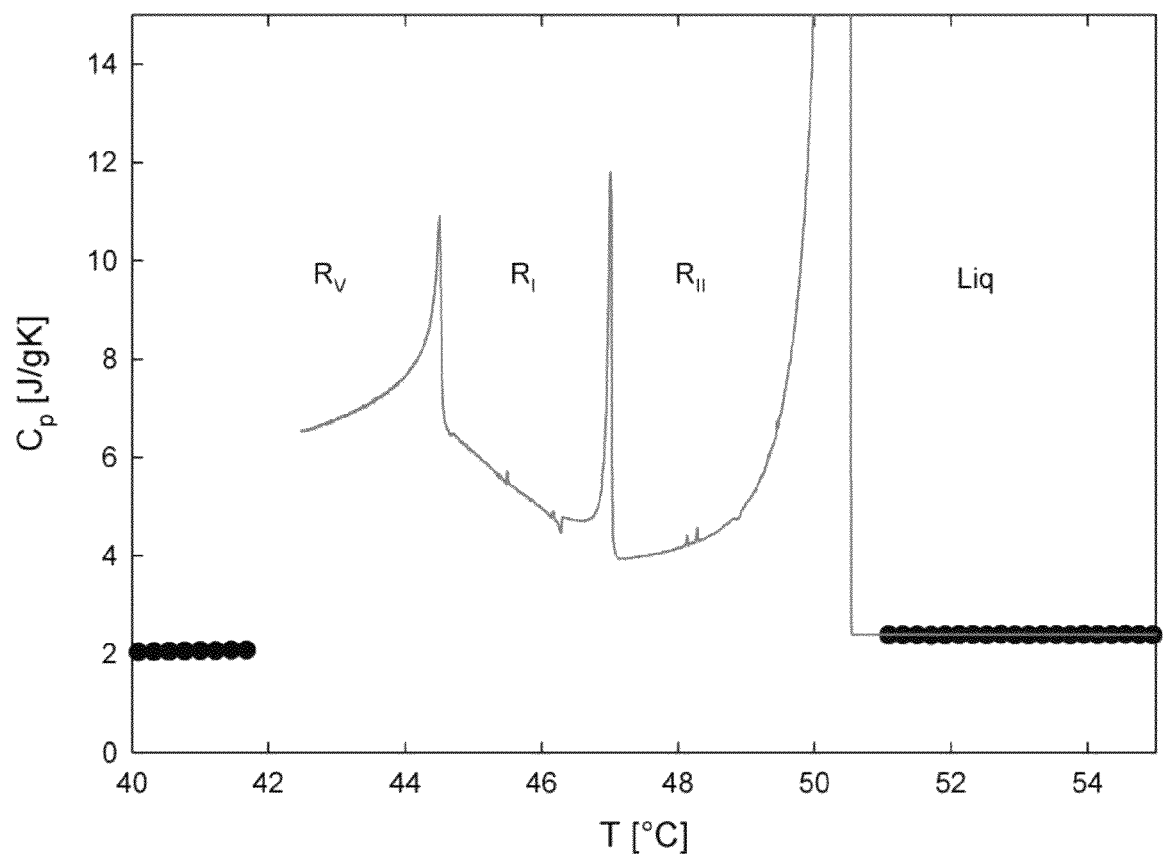

FIG. 8 demonstrates heat capacity $C_p$ as a function of temperature for the same 59 mg sample of tetracosane (C24) from a cooling run with constant negative power. The sample supercooled to about 42° C. and then suddenly solidified. The rotator phases $R_1$ and $R_v$ are metastable and can only be observed when the sample supercools. The solid dots represent heat capacity data of the same sample as obtained running the pASC calorimeter in the heat step mode. Below 42° C. the dots are for the crystal phase and above 51° C. for the liquid phase.

Figure 9A:
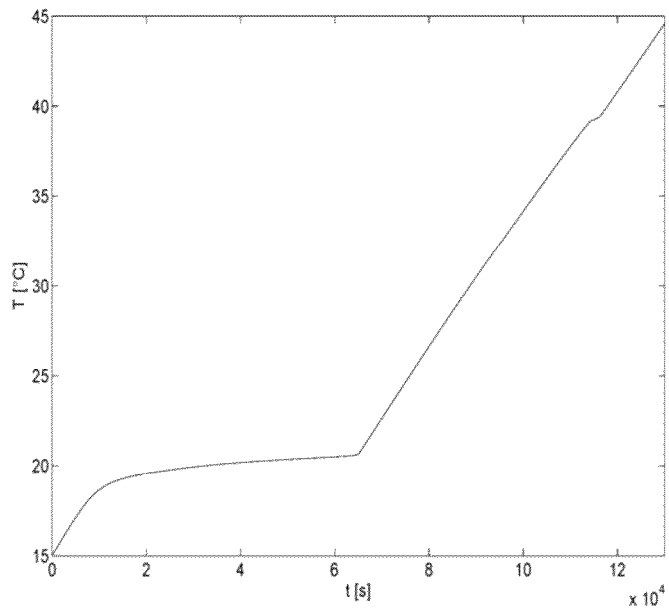
Figure 9B:
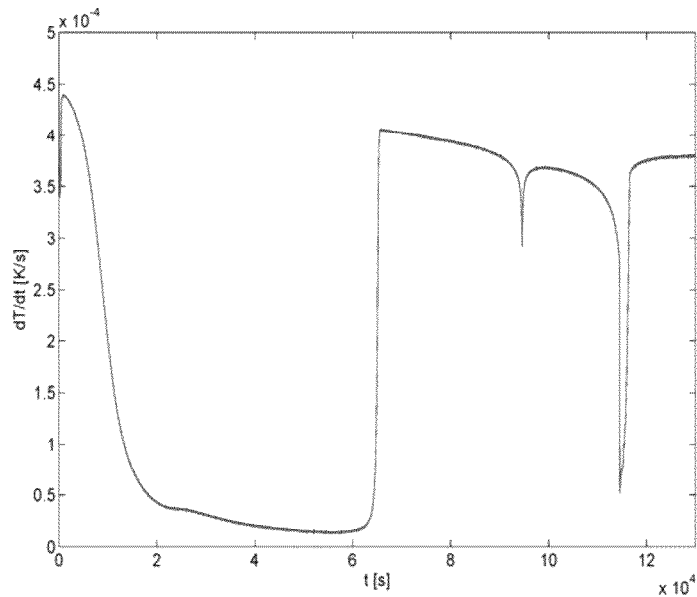

FIG. 9 displays in panel A the recorded temperature data as a function of time T(t) during a heating ran at constant, power for a 57 mg sample of the liquid crystal octyicyanobiphenyl (8CB) over a temperature range covering the crystal-smectic A (Cry-SmA), the smectic A-nematic (SmA-N) and the nematic-isotropic (N-I) transitions and in panel B the time derivative dT/dt of the T(t) results as a function of time.

Figure 10:
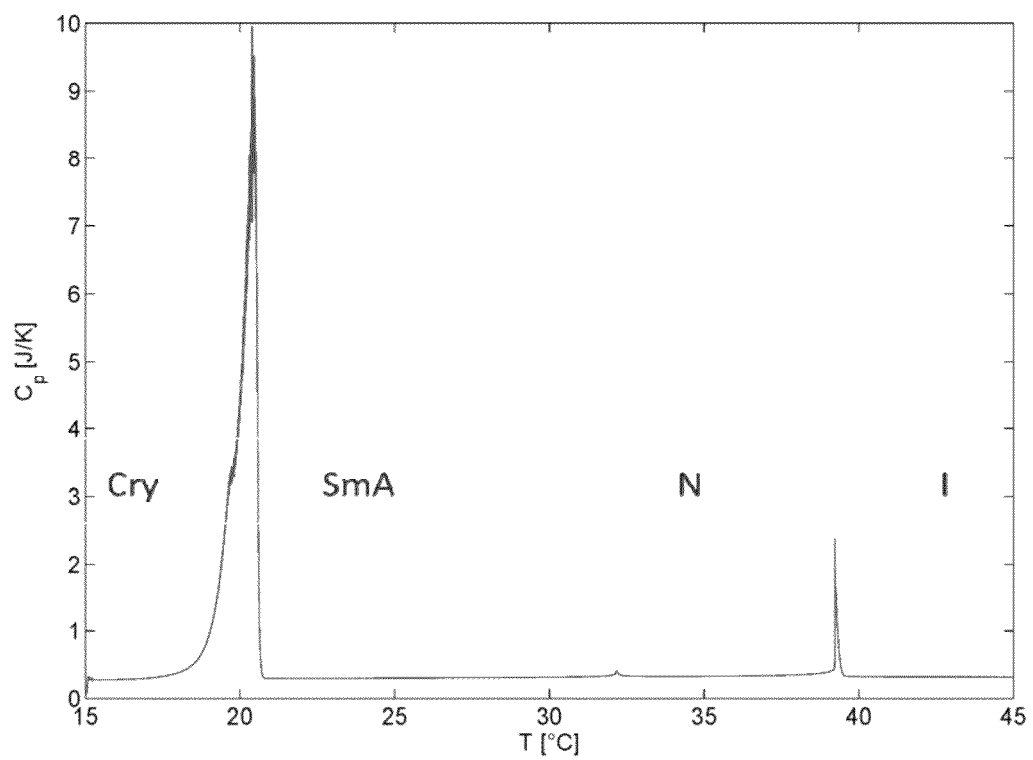

FIG. 10 displays the heat capacity Cp as a function of temperature for the liquid crystal octyicyanobiphenyl (8CB) as derived from the directly recorded temperature and power data as a function of time. Cry: crystal, SmA: smectic A, N: nematic and I: isotropic phases.

Figure 11:
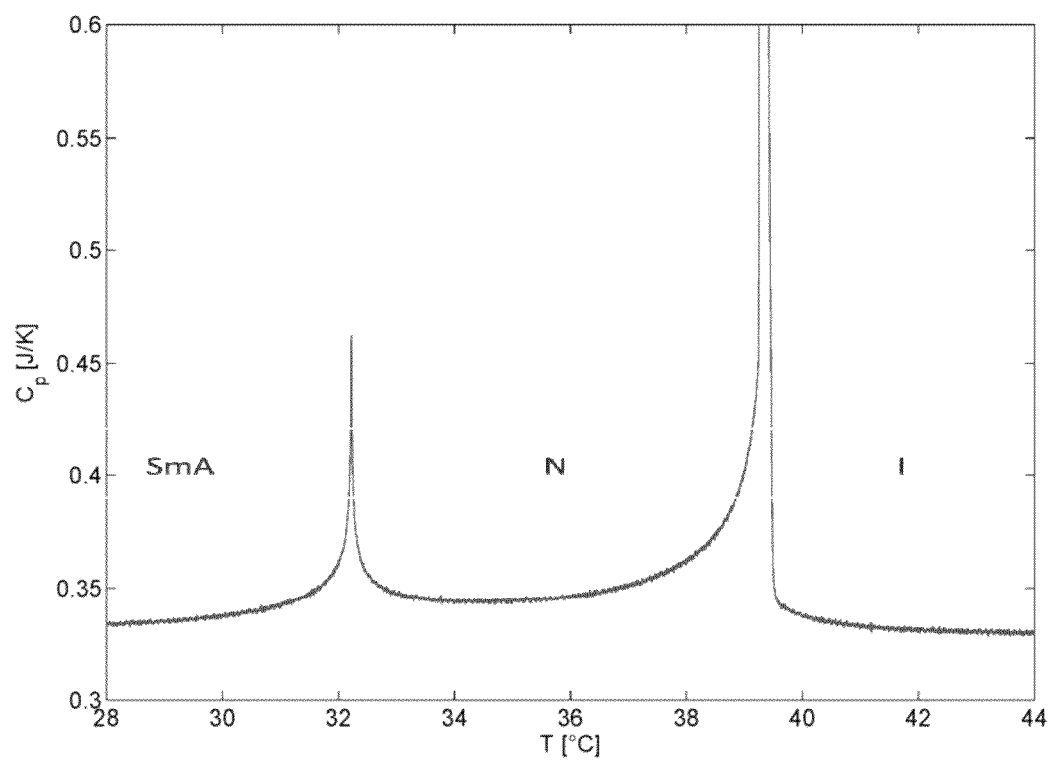

FIG. 11 displays the heat capacity $C_p$ as a function of temperature of the liquid crystal octyicyanobiphenyl covering the smectic A-nematic (SmA-N) and the nematic-isotropic (N-I) transitions.

Figure 12:
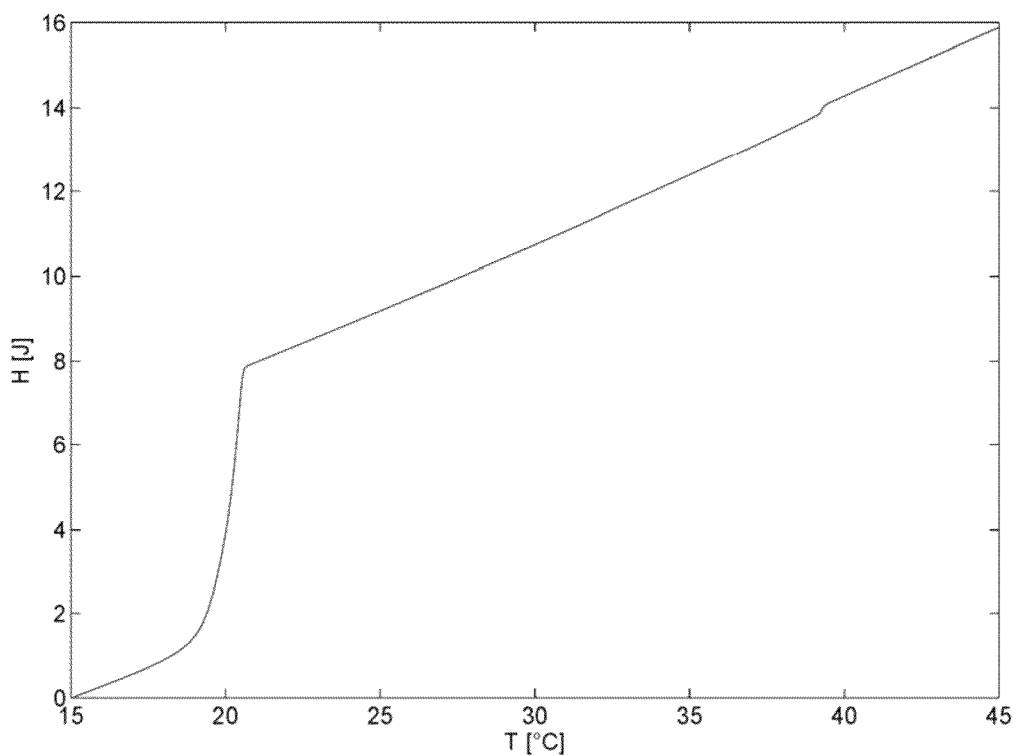

FIG. 12 displays the enthalpy H as function of temperature for the liquid crystal octylcyanobiphenyl (8CB) from the crystal phase at low temperatures to the isotropic phase at high temperatures.

Figure 13:
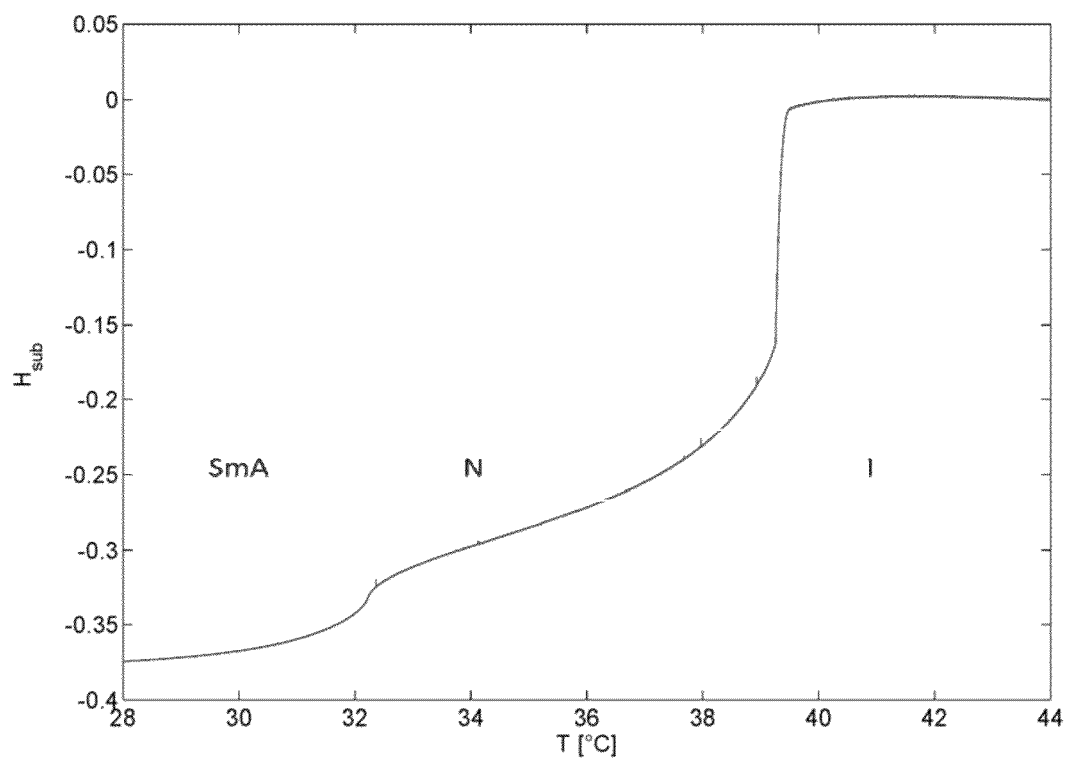

FIG. 13 displays the enthalpy H as function of temperature for the liquid crystal octylcyanobiphenyl (8CB) from the smectic A phase at low temperatures to the isotropic phase at high temperatures.

FIG. 14 displays the details of the enthalpy H variation with temperature near the smectic A-nematic (SmA-N) transition (panel A) and near the nematic-isotropic (N-I) transition (panel B). The SmA-N transition is within experimental resolution second order. The N-I transition is weakly first order with a small latent heat (enthalpy step).

DESCRIPTION OF A PREFERRED EXEMPLARY EMBODIMENT

Figure 1:
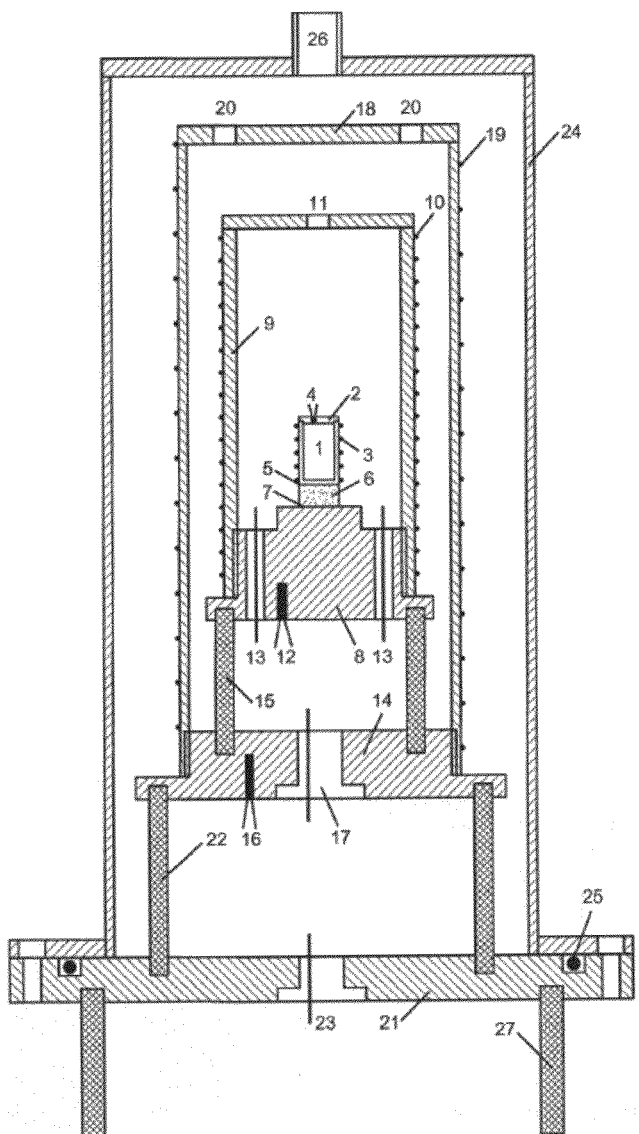
FIG. 1 shows diagrammatically an elevational front view of an exemplary embodiment of a Peltier element based adiabatic scanning calorimeter for simultaneous measurements of heat capacity and enthalpy. Separate elements have been numbered and the numbers have been identified hereunder in the description.
Figure 2:
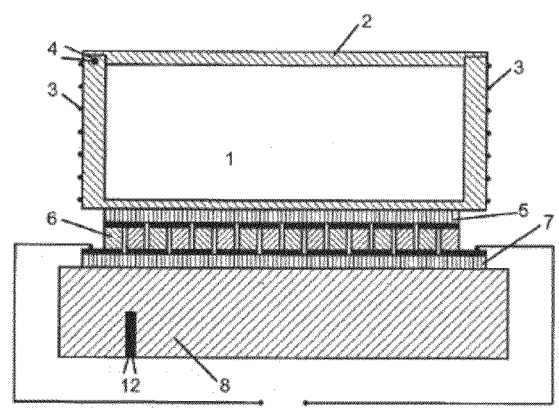
FIG. 2 represents diagrammatically an enlarged elevational front view of the central part of the calorimeter with the (typically liquid) sample [1], sample holder [2], heater [3], temperature sensor [4] on the sample holder [2], Peltier element [6], top [5] and bottom [7] plates of the Peltier element [6], and part of the shield bottom [8] with shield temperature sensor [12].

Referring now specifically to the drawings, a Peltier element based adiabatic scanning calorimeter for simultaneous measurements of heat capacity and enthalpy according to a preferred exemplary embodiment of the present invention is illustrated in FIG. 1, and partly in FIG. 2. In the central part of the calorimeter a sample [1] is contained in a good thermal conducting (e.g. metal) sample holder [2] containing a heating element [3] (e.g. heating wire or thin film heater) and a sensitive temperature sensor [4] (e.g. a thermistor or a Platinum resistance thermometer). The Peltier element is arranged to geometrically position between said at least one plate that contacts the sample holder and at least one plate that contacts the shield for instance the shield bottom [8]. Depending upon the orientation and position, in a logical special orientation of the apparatus as displayed in the FIGS. 1 to 4 (hereby not limiting the invention to a certain special position and proposing the position of the entire apparatus to be exemplary only), the sample holder [2] is positioned in good thermal contact with the top plate [5] of the Peltier element [6]. The sample holder is positioned in good thermal contact with the top plate [5] of the Peltier element [6]. Good thermal contact can e.g. be achieved by soldering, with good thermal conductive varnish, epoxy or paste. For ease of removal of the sample holder thermal paste can preferentially be used. The base plate [7] of the Peltier element is also positioned in good thermal contact with the shield bottom [8]. Good thermal contact can e.g. be achieved by soldering, with good thermal conductive varnish, epoxy or paste. As examples, but not exclusively or limiting, commercially available Peltier Elements of Thermion Company (Odessa, Ukraine) and thin Film Peltier Coolers or thin Film Thermogenerators of Micropelt (Freiburg, Germany) can be and have been used. The shield top [9] is in very good thermal contact with the shield bottom [8] by a sufficiently long screw thread. The shield top [9] has a heater [10] incorporated in the wall. A small hole [11] in the shield is present for possible evacuation or as inert gas inlet. The shield also has its own temperature sensor [12]. The shield bottom also has the necessary electrical feed-troughs [13], The first shield bottom [8] rests on the bottom [14] of a second shield and is thermally insulated by typically three thin rods or tubes [15] with very high thermal resistances. The second shield bottom [14] contains also a temperature sensor [16] and (multipin) electrical feed-troughs [17], In the top part of the second shield [18] a heater [19] is also incorporated. It also as a few holes [20] for evacuation purposes or as inert gas inlets. The top [18] and bottom [14] of the second shield are in very good thermal contact by means of a sufficiently long screw thread. The second shield bottom rests on the bottom [21] of a third shield (outer can) and is thermally insulated by typically three thin rods or tubes [22] with very high thermal resistances. The third shield bottom [21] contains vacuum-tight multipin electrical feed-troughs [23]. The top [24] of the third outer shield and bottom [21] can be vacuum-tightly closed by means of screws and an O-ring [25] in a groove of the bottom [21]. The third shield top [24] (or alternatively shield bottom [21]) contains a connecting tube [26] to a vacuum pumping system or an inert gas inlet system. The bottom of the third (outer) shield [21] is supported by typically three thin rods or tubes [27] with very high thermal resistance. This allows the calorimeter to be place on a table top and if desired surrounded with insulating material. In an alternative exemplary setup the calorimeter is placed in a temperature controlled chamber (stability around ±0.1 K) equipped with heating and cooling units allowing measurements between −60° C. and 150° C. Lower cryogenic temperatures (e. g. to −200° C.) can be achieved by minor design changes and incorporation of the calorimeter in a Dewar system. Proper choice of Peltier elements allows temperatures up to above 200° C.

FIG. 2 gives a more detailed view of a possible sample ceil [2] with heater [3] and temperature sensor [4] and with inside a sample [1] (typically a liquid), on top of the top plate [5] of the Peltier element [6]. The bottom plate [7] of the Peltier element [6] is placed on top of (part of) the bottom [8] of the first shield with the temperature sensor [12] also indicated.

Figure 3:
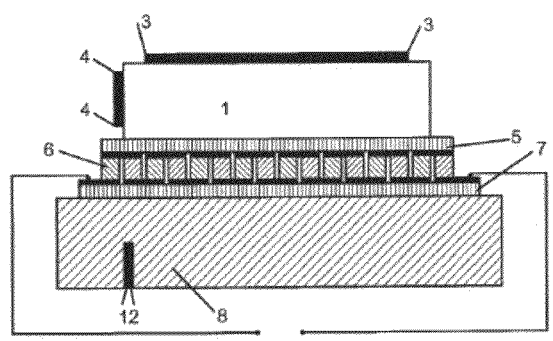
FIG. 3 represents diagrammatically an enlarged elevational front view of the central part of the calorimeter with a solid sample [1], (film) heater [3] on the sample [1], (surface) temperature sensor [4] on the sample [1], Peltier element [6], top [5] and bottom [7] plates of the Peltier element [6], and part of the shield bottom [8] with shield temperature sensor [12].

FIG. 3 gives a more detailed view of an alternative embodiment for a solid sample [1] directly placed on top of the top plate [5] of the Peltier element [6]. A (thin film) heater [3] and a (thin film) temperature sensor [4] are directly attached to the sample [1], The bottom plate [7] of the Peltier element [6] is placed on top of (part of) the bottom [8] of the first shield with the temperature sensor [12] also indicated.

Figure 4:
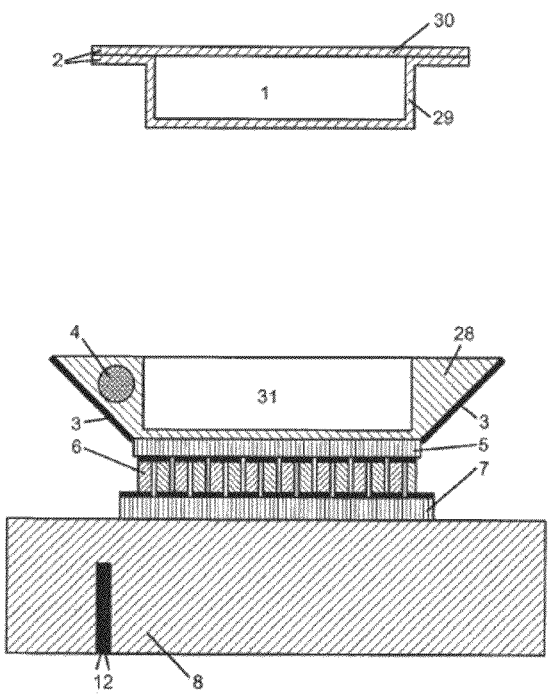
FIG. 4 represents diagrammatically an enlarged elevational front view of the central part of the calorimeter with the (liquid or solid) sample [1], sample holder [2], adapter piece [28] with heater [3] and temperature sensor [4], Peltier element [6], top [5] and bottom [7] plates of the Peltier element [6], and part of the shield bottom [8] with shield temperature sensor [12].

FIG. 4 gives a more detailed view of an alternative embodiment for easy sample [1] and sample holder [2] replacement and no need for heater [3] or sensor [4] removal. On the top plate [5] of the Peltier element [6] an adapter piece [28] of a highly thermal conducting material (e. g. aluminium, silver, copper) is fixed. This adapter piece contains an (embedded) temperature sensor [4] and a (thin film) heater [3], The sample [1] (solid or liquid) is contained in a (thin) small sample holder [2] consisting of a cup [29] and a lid [30] made of thin (soft) metal sheet. The cup [29] and the lid can be pressure closed. The sample holder cup [29] fits tightly in the cavity [31] of the adapter piece [28]. Thermal contact between the sample holder cup [29] and the adapter piece [28] can be further improved by using (a minute quantity of) thermal conducting paste.

Description of the Exemplary Operational Modes and Measurement Control

In this part we refer, in addition to the drawings of FIGS. 1 to 4, also to the drawings of FIG. 5. The same reference numbers in the different drawings of the different figures identify the same or similar elements. The modes 1 and 2 below are the principal operational modes but several other operational modes are possible and described.

Mode 1) A first mode of operation of the calorimeter is at (known) constant heating power P delivered to the heater [3] on the sample holder [2] (in FIGS. 1 and 2), or directly on the sample [1] (in FIG. 3), or on the adapter piece [28] (in FIG. 4), while a zero or negligibly temperature difference with the bottom [8] and top [9] of the first shield is implemented. The desired power is delivered by a DC current source [32] under the control, via a GPIB link [33] or equivalent, of a software program implemented on a personal computer (PC) [34]. The accurate value of the power P is measured by voltage measurements over the resistive heater [3] and over a reference resistor [35] in series with the heater by means of a high-resolution digital multimeter (DMM) [36] equipped with a multiplexer [37]. The negligible temperature difference between sample and first shield is achieved by a software PID control program unit on the PC [34] directing (via the GPIB link [33] or equivalent) the programmable power supply [38] to deliver the necessary heating power to the shield heater [10] in order to keep the output voltage of the Pelier element [6], measured with the DMM [36], always zero during the (scanning) heating run. For stability reasons a different PID control program unit on the PC [34] directs a different programmable power supply [39] to deliver the necessary power to the heater [19] in order to keep the temperature of the second shield top [18] and bottom [14] a few tenths of a degree below that of the first shield [8] and [9]. The temperature difference is obtained from the resistance measurements, with the DMM [36], of the calibrated temperature sensors [12] and [16], For very high resolution and stability of a run the whole calorimeter is placed in a closed chamber [40] equipped with an externally addressable (by the PC [34] via the GPIB link [33]) temperature controlling unit. The temperature of the chamber is controlled in such a way that a fixed temperature difference of a few degrees is maintained between the temperature of the second shield [14], [19] and the outer (third) shield [24], During the whole run the resistance of the calibrated temperature sensor [4] (in good thermal contact with the sample [1]) is measured almost continuously every few seconds with the commercial high resolution digital multimeter [34] (typically 7 or 8 digits resolution). The measured resistance data are converted to temperature and stored together with the measured heating power values. This results in a (long) file of temperature T(t) and P(t) versus time, allowing the direct calculation of the enthalpy H(T) with equation (2) and after numerical differentiation of T(t) with time t, also the calculation of the heat capacity via equation (1).

Mode 2) A second mode of operation of the calorimeter is at constant cooling power P. This is achieved by starting at a desired high temperature and setting and keeping the temperature of the first shield top [9] and bottom [8] always a chosen ΔT (depending on the desired cooling rate) below that of the sample holder [2] and/or sample [1]. The sample holder and/or sample will cool down mainly by thermal conduction through the Peltier element [6] and also by heat exchange with the first shield through radiation and gas conduction (when present). Keeping ΔT between sample and first shield constant by a given negative output voltage of the Peltier element [6] by the software PID control program unit on the PC [34] (controlling the temperature of the first shield) results (with proper calibration) in constant cooling power runs. The temperatures of the second and third shield are controlled in the same way as for the constant heating power mode. The heaters on the sample or the holder or adapter piece are not in use in this cooling mode 2. During the whole run the resistance of the temperature calibrated temperature sensor [4] (in good thermal contact with the sample [1]) is measured almost continuously every few seconds with the commercial high resolution digital multimeter [36] (typically 7 or 8 digits resolution). The measured resistance data are converted to temperature and stored by the PC [34], This results in a (long) file of temperature T(t) and versus time, allowing with the calibrated leaking power P, the direct calculation of the enthalpy H(T) with equation (2) and after numerical differentiation of T(t) with time i, also the calculation of the heat capacity via equation (1).

Mode 3) The calorimeter can also be operated with constant heating power without the presence of the heater [3] or temperature sensor [4] on the sample [1] or the sample holder [2] or on the adapter piece [28], To this end the software controlling unit is programmed in such a way that the power delivered by the power supply [38] to the heater [10] makes that at ail times the temperature of the top [5] of the Peltier is a given amount ΔT below that of the bottom [7], This is realized by maintaining the voltage output of the Peltier element [6] at a preset constant value by the PTD control unit on the PC [34] for the first shield. A constant heat leak trough the Peltier element [6] will heat the sample [1] (and addenda when present). The control setting of the other shields is similar to those of mode 1. Proper calibration of the heat leak will allow to arrive at values for the heating power P in the equations 1 and 2. The necessary temperature T(t) versus time t results can in this mode of operation be obtained by measuring the resistance of the temperature sensor [12]. This results in a (long) file of temperature Tit) versus time, allowing the direct calculation of the enthalpy H(T) with equation (2) and after numerical differentiation of T(t) with time t, also the calculation of the heat capacity via equation (1).

Mode 4) The calorimeter can also be operated with constant cooling power without the presence of the heater [3] or temperature sensor [4] on the sample [1] or the sample holder [2] or on the adapter piece [28], To this end the software controlling unit is programmed in such a way that the power delivered by the power supply [38] to the heater [10] makes that at ail times the temperature of the top [5] of the Peltier is a given amount ΔT above that of the bottom [7], This is realized by maintaining the voltage output of the Peltier element [6] at a preset constant value by the PID control unit on the PC [34] for the first shield. A constant heat leak trough the Peltier element will cool the sample (and addenda when present). Proper calibration of the heat leak will allow to arrive at values for the heating power P in the equations (1) and (2). The necessary temperature T(t) versus time t results can in this mode of operation be obtained by measuring the resistance of the temperature sensor [12]. This results in a (long) file of temperature T(t) versus time, allowing the direct calculation of the enthalpy H(T) with equation (2) and after numerical differentiation of T(t) with time t, also the calculation of the heat capacity via equation (1).

Mode 5) Instead of carrying out heating runs with constant heating power (mode 1) it is also possible to do runs at a constant heating rate T (similar to a heating run in a DSC). In this mode a constant power is delivered by the power supply [38] to the heater [10] on the first shield while the temperature of the second shield is kept at a fixed difference below that of the first one. The temperature difference between sample and the first shield is kept zero by controlling the voltage output of the Peltier element [6] to zero at all times by adjusting the current delivered by the DC current source [32] to the heater [3]. The settings of the T-controlled chamber [40] containing the calorimeter are as for mode 1. The constant rate f can be obtained by measuring T(t) of the first shield with the temperature sensor [12]. The changing power P(t) in heater [3] on the sample is measured with the DMM [36]. From the power Pit) and the rate T the heat capacity $C_p(T)$ can be directly calculated with equation (1).

Mode 6) Instead of carrying out cooling runs with constant cooling power (mode 2) it is also possible to do runs at a constant cooling rate T (similar to a cooling run in a DSC). In this mode the temperature of the second shield is kept at a fixed difference below that of the first one. The temperature of the (cooling) is sample maintained a constant ΔT above that of the first shield by controlling the voltage output of the Peltier element [6] to preset fixed value at all times by adjusting the current delivered by the DC current source [32] to the heater [3], The settings of the T-controlled chamber [40] containing the calorimeter are as for mode 2. The constant rate T can be obtained by measuring T(i) of the first shield with the temperature sensor [12]. The changing power P(t) in heater [3] on the sample is measured with the DMM [36], From the power P(t) and the rate f the heat capacity $C_p(T)$ can be directly calculated with equation (1).

Mode 7) This Peltier element based calorimeter can also be operated as a classical (Nernst type) heat pulse step calorimeter. In this mode of operation an adapted software controlling program starts by stabilizing the temperature of the first shield at a preset fixed value by controlling the power input to the heater [10] on the first shield. The temperature of the second shield is kept at all times at a temperature very near but below that of the first shield. The temperature of the sample [1] (plus addenda) is let to evolve freely until it reaches the stable constant value (measured with T-sensor [4]) over a sufficiently long time. Subsequently, during a relatively short time power is delivered by the DC source [32] to the heater [3]. During the heating pulse operation the software PID program unit forces, via power delivery by the power supply [38], the temperature of the first shield to follow the temperature of the sample, while also the second shield temperature is made to follow the induced temperature changes of sample and first shield. After the heat pulse the temperature of the sample (and addenda) is recorded until a steady-state is reached over a sufficiently long time allowing the determination the temperature increase ΔT during the pulse. From ΔT, the power P during the pulse and the pulse duration time Δt the heat capacity is calculated with C=P·Δt/ΔT.

Mode 8) As a modification of mode 1 the calorimeter can also be operated in a power modulated (scanning) heating mode. For this purpose the settings are identical or very similar to those described for mode 1. However, instead of supplying a constant power to heater [3] a small AC signal (of appropriate frequency) is supper imposed on the constant heating power to heater [3]. This can be achieved in the software program controlling the current source [32], or by using a programmable function generator combining an AC signal with a DC offset. In the measured temperature time evolution T(t) with the T-sensor [4], the AC and DC components can be separated in a software program unit on the PC [34], It is also possible to separate the AC component directly using lock-in detection. The amplitude of the AC signal directly leads to the heat capacity C(T) while the DC component is used to obtain the temperature dependence of the enthalpy H(T).

Mode 9) As a modification of mode 2 the calorimeter can also be operated in a power modulated (scanning) cooling mode. For this purpose the settings are identical or very similar to those described for mode 2. In this case a small (compared to the negative cooling power) AC signal (of appropriate frequency) is supplied to heater [3]. This can be achieved by using a programmable function generator instead of the current source [32], In the measured temperature time evolution T(t) with the T-sensor [4] the AC and DC components can be separated in a software program unit on the PC. It is also possible to measure the AC component directly using lock-in detection. The amplitude of the AC signal directly leads to the heat capacity C(T) while the DC component is used to obtain the temperature dependence of the enthalpy H(T).

EXAMPLES

Example 1

Enthalpy and Heat Capacity of First Order Transitions of an N-Alkane

Results as obtained with a Peltier element based Adiabatic Scanning Calorimeter (pASC) for phase transitions in the normal alkane tetracosane (C24) are displayed in the FIGS. 5 to 7 and explained in their legends.

Example 2

Enthalpy and Heat Capacity of First and Second Order Phase Transitions in a Liquid Crystal Results as obtained with a Peltier element based Adiabatic Scanning Calorimeter (pASC) for first and second order phase transitions in the liquid crystal octylcyanobiphenyl (8CB) are displayed in the FIGS. 9 to 14 and explained in their legends.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

It will be apparent to those skilled in the art that various modifications and variations can be made in the choice of the type and numbers of Peltier elements and in its implementation in the calorimeter and in using different numbers of shields and their temperature measurements and control approaches of the present invention and in construction of the system and method without departing from the scope or spirit of the invention. Examples of such modifications have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An adiabatic scanning calorimeter apparatus comprising:
    a sample on a sample holder,
    at least a first heater arranged on the sample or on the sample holder and adapted for heating the sample and the sample holder,
    at least one thermal or adiabatic shield surrounding the sample or the sample holder,
    a first temperature sensor arranged on the sample or on the sample holder for measuring a temperature thereof and/or a temperature sensor arranged on said thermal or adiabatic shield for measuring a temperature of the shield;
    a second heater surrounding the first heater and said thermal or adiabatic shield configured for heating the thermal or adiabatic shield;
    at least one Peltier element placed between the sample or the sample holder and the shield, and making; good mechanical and thermal contacts with the sample or the sample holder and the shield, configured to be used as a differential thermometer;
    means for determining the temperature of the sample holder using the first temperature sensor, and for determining a temperature difference between the shield and the sample holder using the Peltier element, and means for powering the first and second heater in such a way that a constant preset temperature difference of a few tenths of a degree Celsius or a zero temperature difference between the sample or the sample holder and the shield is maintained,
    thereby allowing simultaneous measurements of the temperature dependence of heat capacity and enthalpy of solid or liquid samples and phase transitions therein.

2. The apparatus of claim 1, further comprising at least one first plate that contacts the sample or the sample holder, and at least one second plate that contacts the shield,
    and wherein the Peltier element is arranged in a geometric position between said at least one first plate and said at least one second plate.

3. The apparatus of claim 1, wherein the Peltier element has a top plate and a base plate and wherein the adiabatic shield has a bottom, and wherein the sample holder is positioned in thermal conductive contact with the top plate of the Peltier elements and
    wherein said base plate of the Peltier element is also positioned in good thermal contact with the said shield bottom.

4. The apparatus of claim 1, wherein the at least one thermal or adiabatic shield surrounding the sample or the sample holder further comprises at least one second temperature sensor arranged on said thermal or adiabatic shield.

5. The apparatus of claim 1, wherein the at least one thermal or adiabatic shield surrounding the sample or sample holder comprises at least one temperature sensor arranged in the thermal or adiabatic shield or in a bottom of the thermal adiabatic shield.

6. The apparatus of claim 1, wherein the Peltier element is operated as either a cooling or thermo-generator function.

7. The apparatus of claim 1, wherein the Peltier element is operated as a zero instrument.

8. The apparatus of claim 1, wherein the mechanical contact is suitable for heat transfer.

9. The apparatus of claim 1, wherein the first temperature sensor is a thermistor.

10. The apparatus of claim 1, wherein the first temperature sensor is a Platinum resistance thermometer.

11. The apparatus of claim 1, further comprising an adapter piece, and wherein the first temperature sensor is placed on said adapter piece and on the thermal or adiabatic shield.

12. The apparatus of claim 1, wherein the sample is a liquid in the sample holder.

13. The apparatus of claim 1, wherein the sample is a solid in the sample holder or a solid in direct thermal contact with the Peltier element.

14. The apparatus of claim 1, further comprising an adapter piece, the sample holder being placed in the adapter piece.

15. The apparatus of claim 1, wherein the apparatus is provided with a controller with a servo systems adapted to maintain almost perfect equality of the sample and thermal or adiabatic shield temperatures in a heating mode, based on readings of the Peltier element.

16. The apparatus of claim 1, wherein the controller and the Peltier element maintain a temperature differences between the sample and the surrounding thermal or adiabatic shield zero or at a preset fixed value during a temperature scanning operation.

17. The apparatus of claim 1, adapted to keep a temperature difference between the sample and the thermal or adiabatic shield constant.

18. The apparatus of claim 1, wherein the Peltier element maintains a temperature difference between the thermal or adiabatic shield and the sample at zero or at a constant temperature difference.

19. The apparatus of claim 1, adapted so that the apparatus when operational in a heating mode, equality of the temperatures of the sample and the surrounding thermal shield.

20. The apparatus of claim 1, further comprising an assembly of multiple units, each unit including:
- a sample holder,
- a thermal or adiabatic shield, and
- an active Peltier element that mechanically contacts a sample or the sample holder and the thermal or adiabatic shield, wherein the Peltier element is configured to simultaneously measure a temperature dependence of heat capacity and the enthalpy of a sample and of a phase transitions therein.

21. The apparatus of claim 20, wherein the multiple units are connected to a signal processor and input signals from each unit are fed to said signal processor with a controller adapted to control the Peltier elements.

22. The apparatus of claim 1, where the sample and the thermal or adiabatic shield are surrounded by additional thermal shields, each with temperature sensors and heaters under control of a servo system on a processor.

23. The apparatus of claim 1, wherein a constant heating power is delivered to the sample and/or to the sample holder.

24. The apparatus of claim 1, wherein a constant cooling power is delivered to the sample and/or to the sample holder.

25. The apparatus of claim 1, wherein a heat transfer through the Peltier element is used to heat the sample.

26. The apparatus of claim 1, wherein a heat transfer through the Peltier element is used to cool the sample.

27. The apparatus of claim 1, wherein a heating power delivered to the sample is modulated.

28. The apparatus of claim 1, wherein a cooling power delivered to the sample is modulated.

29. The apparatus of claim 1, wherein the thermal or adiabatic shield has a hole for allowing the calorimeter to be evacuated or to be filled with an inert gas.

30. The apparatus of claim 1, wherein the constant preset temperature difference is less than 3 tenths of a degree Celsius.

31. A method of use of the adiabatic scanning calorimeter according to claim 1 for simultaneously measuring a thermodynamic equilibrium of the heat capacity and enthalpy of phase transition of a sample.

32. The method according to claim 31, wherein said phase transitions are near fluctuations dominated phase transitions.

33. A method of use of the adiabatic scanning calorimeter according to claim 1 for separation between pretransitional enthalpy of transition variations and true latent heats at first-order or weakly first-order phase transitions.

34. A method of use of the adiabatic scanning calorimeter according to claim 1 for simultaneously measuring heat capacity and enthalpy of phase transitions of a sample.

35. A method of use of the adiabatic scanning calorimeter according to claim 1, to yield accurate absolute values of specific heat of the sample by using scanning rates below 0.2 Ks-1.

36. A method of use of the adiabatic scanning calorimeter according to claim 1, to discriminate between second-order continuous phase transitions and weakly first-order phase transition of a sample.

37. A method of use of the adiabatic scanning calorimeter according to claim 1, for defining or characterizing a phase transition of a material as influence of a production process.

38. A method of use of the adiabatic scanning calorimeter according to claim 1, for defining or characterizing of a phase transition in liquid crystals or biological systems or cell membranes.

39. A method of use of the adiabatic scanning calorimeter according to claim 1, for defining a suitable material for a defined property.

40. A method of use of the adiabatic scanning calorimeter according to claim 1, for selecting a suitable material for a use.

41. A method of monitoring an energy content of a condensed matter sample using an adiabatic scanning calorimeter according to claim 1, comprising the steps of:
- quantifying thermodynamic equilibrium simultaneously with a temperature dependence of the heat capacity and of enthalpy of the sample and of phase transitions therein;
- delivering constant heating or cooling power to the sample; and
- keeping a temperature difference between the sample and the surrounding thermal shield at zero or at a preset fixed value using said Peltier element during a temperature scan over a broad range.

* * * * *